(12) United States Patent
Nakata

(10) Patent No.: US 8,157,734 B2
(45) Date of Patent: Apr. 17, 2012

(54) ULTRASONIC DIAGNOSTIC APPARATUS AND ULTRASONIC DIAGNOSTIC METHOD

(75) Inventor: Kazuhito Nakata, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 1018 days.

(21) Appl. No.: 11/254,052

(22) Filed: Oct. 20, 2005

(65) Prior Publication Data

US 2006/0100515 A1    May 11, 2006

(30) Foreign Application Priority Data

Oct. 22, 2004    (JP) ................................. 2004-308642

(51) Int. Cl.
*A61B 8/06* (2006.01)
(52) U.S. Cl. .......................... 600/440; 600/437; 600/441
(58) Field of Classification Search .................. 600/407, 600/437, 440, 441, 443; 73/602
See application file for complete search history.

(56) References Cited

U.S. PATENT DOCUMENTS

| 5,501,223 | A  | * | 3/1996  | Washburn et al. | ............ 600/455 |
| 6,464,637 | B1 | * | 10/2002 | Criton et al.   | ............ 600/441 |
| 6,508,766 | B2 |   | 1/2003  | Sato et al.     |                      |

FOREIGN PATENT DOCUMENTS

| JP | 6-7348      | 1/1994 |
| JP | 2002-143168 | 5/2002 |

* cited by examiner

*Primary Examiner* — Tse Chen
*Assistant Examiner* — Peter Luong
(74) *Attorney, Agent, or Firm* — Oblon, Spivak, McClelland, Maier & Neustadt, L.L.P.

(57) ABSTRACT

An ultrasonic diagnostic apparatus comprises a transmission and reception unit, a blood flow image generating unit, a Doppler spectrum image generating unit and a scanning sequence setting unit. The transmission and reception unit transmits first and second ultrasonic waves to an object and receive first and second echo signals from the object. The blood flow image generating unit generates a blood flow image from the first echo signals. The Doppler spectrum image generating unit generates a Doppler spectrum image from the second echo signals. The scanning sequence setting unit sets up a scanning sequence with mutual transmission and reception of the first and the second ultrasonic waves. The scanning sequence setting unit alters the scanning sequence into one having a modulated number of ensembles so as to make a frame rate of the blood flow image beyond a predetermined preset value.

14 Claims, 15 Drawing Sheets

ULTRASONIC DIAGNOSTIC APPARATUS AND ULTRASONIC DIAGNOSTIC METHOD

BACKGROUND OF THE INVENTION

1. Field of the Invention

The present invention relates to an ultrasonic diagnostic apparatus and an ultrasonic diagnostic method for obtaining an ultrasonic image by transmission and reception of an ultrasonic wave, and more particularly, to an ultrasonic diagnostic apparatus and an ultrasonic diagnostic method for displaying a blood flow image and a Doppler spectrum image simultaneously or almost simultaneously at least.

2. Description of the Related Art

In an observation of an object using an ultrasonic diagnostic apparatus, an operation mode called a triplex mode is used. The triplex mode is a composite mode for displaying a two dimensional configuration image, a two dimensional blood flow image, and a Doppler spectrum image simultaneously or substantially simultaneously.

The two dimensional configuration image is a configuration image generated by converting the intensity of reflected ultrasonic waves to luminance. The two dimensional blood flow image is a two dimensional color image of blood flow generated by extracting a Doppler shift (frequency shift) caused by blood flow, and is overlaid on the two dimensional configuration image by color mapping (color flow mapping). The Doppler spectrum image is a graph showing a change over time in Doppler shift of ultrasonic waves caused by blood flow.

That is, in the triplex mode, a position of a blood vessel and blood flow therein are specified in a two dimensional configuration image and a two dimensional blood flow image, and a blood flow rate is measured in a Doppler spectrum image. In order to display the two dimensional blood flow image and the Doppler spectrum image substantially simultaneously, transmission/reception of ultrasonic waves to obtain the two dimensional blood flow image and transmission/reception of ultrasonic waves to obtain the Doppler spectrum image need to be alternately performed. As a scanning method in the triplex mode, Doppler interleaved scanning is known (see, for example, Japanese Patent Application (Laid-Open) No. 6-7348).

The Doppler interleaved scanning is a method. for scanning an object by alternately performing scanning for a two dimensional configuration image (hereinafter called "B mode scanning") or scanning for a color two dimensional blood flow image (hereinafter called "CFM mode scanning") and scanning for a Doppler spectrum image (hereinafter called "D mode scanning") on a one-by-one basis over time. In the CFM mode scanning, transmission/reception of ultrasonic waves is performed a plurality of times sequentially in the same scanning line in order to remove a clutter component. The number of repetitions of transmission/reception of ultrasonic waves in the same scanning line is called a number of ensemble.

In the Doppler interleaved scanning, B mode scanning or CFM mode scanning is sandwiched between D mode scannings. Therefore, in transmission/reception of ultrasonic waves performed in D mode scanning, pulse-repetition frequency (DpPRF) cannot be set at high. When the DpPRF cannot be set at high, aliasing occurs in the Doppler spectrum image when high-rate blood flow is detected.

In order to overcome this problem, a scanning method called "Doppler segmented scanning" may be used. In this scanning method, B mode scanning or CFM mode scanning and D mode scanning are alternately performed over time in respective groups of beams. In other words, in the Doppler segmented scanning, transmission/reception of ultrasonic waves is alternately performed while distinguishing a B/CFM segment where B mode scanning or CFM mode scanning is continuously performed for a predetermined time period and a D segment where D mode scanning is continuously performed for a predetermined time period. By repeating these two segments, one frame of a two dimensional configuration image is created (see, for example, Japanese Patent Application (Laid-Open) No. 2002-143168).

In the Doppler segmented scanning, DpPRF can be set at high in a segment of D mode scanning. Therefore, aliasing does not occur even in a high-rate blood flow and a favorable waveform can be obtained in a Doppler spectrum image.

When the Doppler segmented scanning is used in the triplex mode, a time ratio between a B/CFM segment and a D segment must be 1:2 or more. In the B/CFM segment, D mode scanning is not performed and thus a gap occurs in a Doppler spectrum image during this time period. This gap is complemented by using data collected in the D segment. Considering a complementation accuracy of the Doppler spectrum image, the time ratio should be 1:2 or more.

However, when the time ratio is 1:2 or more, the frame rate is ⅓ or less compared to that in a composite mode of a two dimensional configuration image and a two dimensional blood flow image. This is because, since neither B mode scanning nor CFM mode scanning is performed in a D segment, the frame rate decreases in accordance with the applied D segment.

Consequently, in the triplex mode, high-rate blood flow can be detected by using the Doppler segmented scanning but an increase in complementation accuracy of a Doppler spectrum image and an increase in frame rate cannot be achieved at the same time.

That is, in an ultrasonic diagnosis apparatus that displays at least a two dimensional blood flow image and a Doppler spectrum image simultaneously or substantially simultaneously, it is difficult to achieve the following three elements at the same time: an adequate detection of high-rate blood flow; an increase in complementation accuracy of a Doppler spectrum image; and an increase in frame rate.

SUMMARY OF THE INVENTION

The present invention has been made in light of the conventional situations, and it is an object of the present invention to provide an ultrasonic diagnostic apparatus and an ultrasonic diagnostic method which prevent the deterioration of a frame rate with maintaining the complement accuracy of a Doppler spectrum image and the satisfactory detection of a blood flow having a high flow velocity in case of displaying the blood flow image and the Doppler spectrum image simultaneously or almost simultaneously at least in the technology of an ultrasonic diagnosis.

The present invention provides an ultrasonic diagnostic apparatus comprising: a transmission and reception unit configured to transmit first ultrasonic waves for obtaining a blood flow image and second ultrasonic waves for obtaining a Doppler spectrum image to an object and receive first echo signals corresponding to the first ultrasonic waves and second echo signals corresponding to the second ultrasonic waves from the object; a blood flow image generating unit configured to generate the blood flow image by subjecting the first echo signals to processing including auto-correlation processing; a Doppler spectrum image generating unit configured to generate the Doppler spectrum image in accordance with the second echo signals; a scanning sequence setting unit configured to set up a scanning sequence for displaying the blood flow image and the Doppler spectrum image simultaneously substantially with mutual transmission and reception of the first ultrasonic waves and the second ultrasonic waves, the scanning sequence setting unit being configured to alter into the scanning sequence one having a modulated number of ensembles according to transmission and reception of the first ultrasonic waves so as to make a frame rate of the blood flow image beyond a predetermined preset value, in an aspect to achieve the object.

The present invention also provides an ultrasonic diagnostic method comprising steps of: setting up a scanning sequence for displaying a blood flow image and a Doppler spectrum image of an object simultaneously substantially with mutual transmission and reception of first ultrasonic waves for obtaining the blood flow image and second ultrasonic waves for obtaining the Doppler spectrum image; transmitting the first ultrasonic waves and the second ultrasonic waves to the object in accordance with the scanning sequence and receiving first echo signals corresponding to the first ultrasonic waves and second echo signals corresponding to the second ultrasonic waves from the object; generating the blood flow image by subjecting the first echo signals to processing including auto-correlation processing; generating the Doppler spectrum image in accordance with the second echo signals; altering the scanning sequence into one having a modulated number of ensembles according to transmission and reception of the first ultrasonic waves so as to make a frame rate of the blood flow image beyond a predetermined preset value, in an aspect to achieve the object.

With the ultrasonic diagnostic apparatus and the ultrasonic diagnostic method as described above, it is possible to maintain a satisfactory frame rate even if alternation leading to reduce a frame rate of an blood flow image is performed.

DESCRIPTION OF THE PREFERRED EMBODIMENTS

An ultrasonic diagnostic apparatus and an ultrasonic diagnostic method according to preferred embodiments of the present invention will be described in further detail below with reference to the accompanying drawings.

1. First Embodiment

Figure 1:
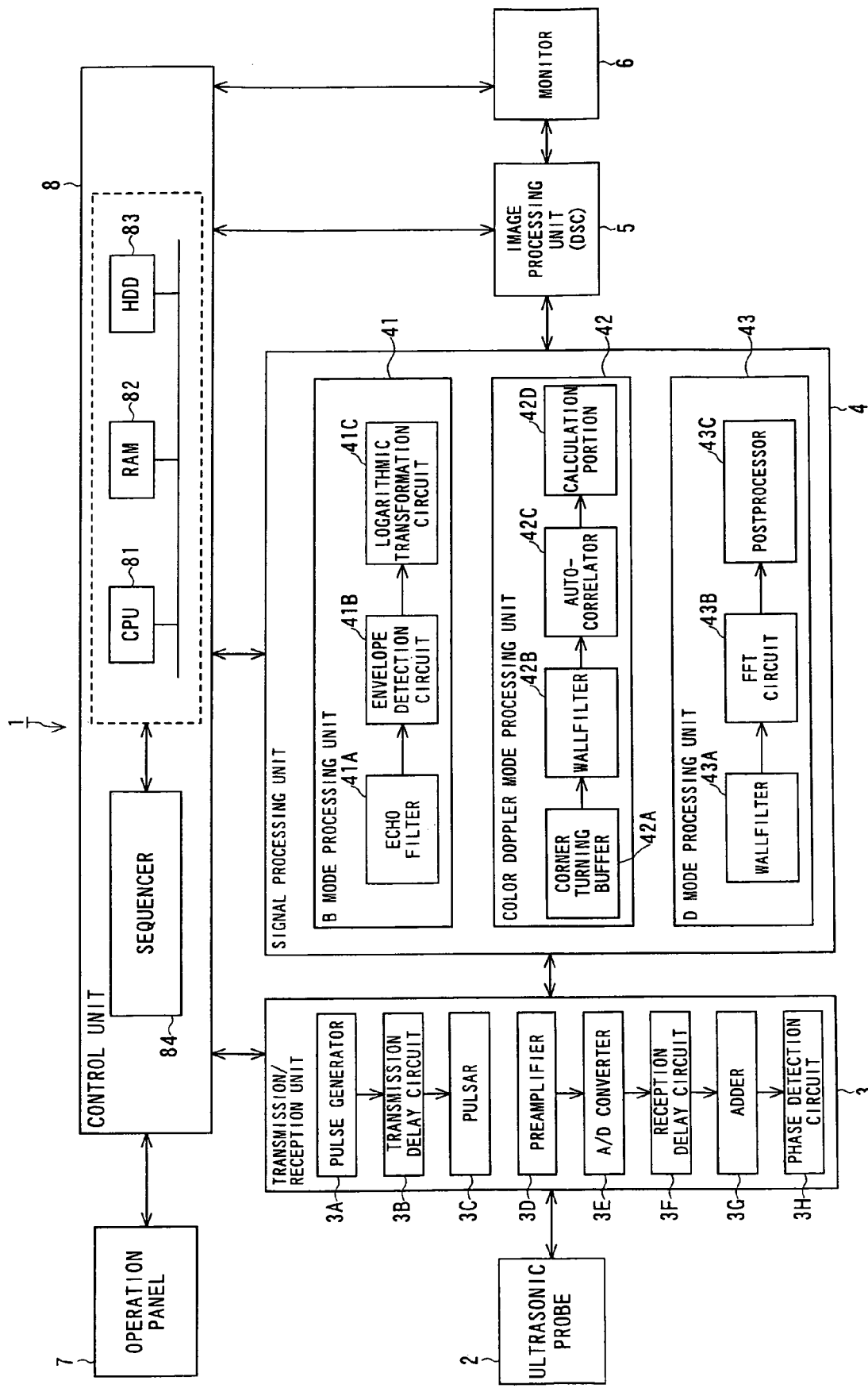
FIG. 1 is a block diagram showing each of first to forth embodiments of ultrasonic diagnostic apparatuses.

FIG. 1 is a block diagram showing a first embodiment of an ultrasonic diagnostic apparatus. An ultrasonic diagnostic apparatus 1 includes an ultrasonic probe 2 and a monitor 6. The ultrasonic probe 2 transmits and receives an ultrasonic wave to and from an object. The monitor 6 displays a two-dimensional configuration image, a two-dimensional blood-flow image and a Doppler spectrum image obtained by transmission and reception of ultrasonic waves. The ultrasonic diagnostic apparatus 1 also includes a transmission/reception unit 3, a signal processing unit 4 and an image processing unit 5, serving as a unit for several processing including signal processing. The transmission/reception unit 3, the signal processing unit 4 and the image processing unit 5 are arranged between the ultrasonic probe 2 and the monitor 6. The ultrasonic diagnostic apparatus 1 also includes a control unit 8 for controlling each of the elements 2, 3, 4, 5 and 6. The control unit 8 communicates with an operation panel 7.

The ultrasonic probe 2 has arrayed piezoelectric transducers, such as piezoelectric ceramics. The ultrasonic probe 2 functions as a transmitter/receiver to transmit/receive ultrasonic waves. When the piezoelectric transducers thereof receive voltage pulses from the transmission/reception unit 3, the ultrasonic probe 2 generates ultrasonic beams, transmits the ultrasonic beams to an object (not shown), receives reflected ultrasonic waves, and converts the reflected ultrasonic waves to echo signals.

The transmission/reception unit 3 includes a transmission part and a reception part. The transmission part has a pulse generator 3a, a transmission delay circuit 3b and a pulsar 3c at least. The reception part has a preamplifier 3d, an A/D (analog to digital) converter 3e, a reception delay circuit 3f, an adder 3g and a phase detection circuit 3h.

The pulse generator 3a controls transmission pulse signal of transmission voltage pulses, generates transmission pulse signals having a pulse width in accordance with each mode, and transmits the pulse signals to the transmission delay circuit 3b. The transmission delay circuit 3b determines a scanning direction of ultrasonic beams and delays application of a transmission pulse signals for every piezoelectric transducer so as to cause a time difference. The pulsar 3c applies a transmission voltage pulse to each piezoelectric transducer at the transmission pulse timing received from the transmission delay circuit 3b.

The preamplifier 3d amplifies an echo signal. The A/D converter 3e converts the amplified signal to a digital signal. The reception delay circuit 3f and an adder 3g delay and add signals from the respective transducers to generate a single signal. A phase detection circuit 3h shifts a desired center frequency of the signal from the adder 3g to 0 Hz and detects a quadrature phase of the signal, and then transmits the detected signal to the signal processing unit 4.

The signal processing unit 4 functions as a generation processing unit to receive signals from the transmission/reception unit 3 and execute signal processing to generate each image.

A B mode processing unit 41 includes an echo filter 41a, an envelope detection circuit 41b and a logarithmic transformation circuit (LOG) 41c. The B mode processing unit 41 performs signal processing (hereafter, called "B mode signal processing") for generating a two-dimensional configuration image. The echo filter 41a filters a frequency-shifted signal received from the transmission/reception unit 3 using a low-pass filter. The envelope detection circuit 41b detects an envelope and obtains an envelope detection signal. The LOG 41c performs logarithmic transformation on the envelope detection signal. With this process, data of a two dimensional configuration image is generated and the data is transmitted to the image processing unit 5.

A color Doppler mode processing unit 42 includes a corner turning buffer 42a, a wall filter 42b, an auto-correlator 42c and a calculation portion 42d. The color Doppler mode processing unit 42 performs signal processing (hereafter, called "CFM mode signal processing") for generating a two-dimensional blood flow image. The corner turning buffer 42a temporarily stores data rows of the quadrature-detected signal from the phase detection circuit 3h and then performs sorting. The wall filter 42b reads the data rows stored in the corner turning buffer 42a in a predetermined order and removes a clutter component of the signal by using a predetermined filter bandwidth. The auto-correlator 42c performs two dimensional Doppler signal processing in real time so as to analyze the frequency of the signal. The calculation portion. 42d includes an average rate calculation portion, a dispersion calculation portion, and a power calculation portion, which calculate data of a two dimensional blood flow image: an average Doppler shift frequency, a dispersion value, and a blood flow power, respectively. For example, the calculation portion 42d converts a blood flow rate component contained in the signal to corresponding color information.

A D mode processing unit 43 includes a wall filter 43a, an FFT (Fast Fourier Transform) circuit 43b and a postprocessor 43c. The D mode processing unit 43 performs signal processing (hereafter, called "D mode signal processing") for generating a Doppler spectrum image. The wall filter 43a removes a clutter component contained in a quadrature-detected signal. The FFT circuit 43b performs frequency analysis on the quadrature-detected signal from which a clutter component has been removed so as to obtain spectrum data. The spectrum data is processed by the postprocessor 43c and is then transmitted to the image processing unit 5.

The image processing unit 5 includes a DSC (digital scan converter). The image processing unit 5 converts each data outputted from the B mode processing unit 41, the color Doppler mode processing unit 42 and the D mode processing unit 43 to image data which can be displayed on the monitor 6 and gives the converted image data to the monitor 6.

Figure 3:
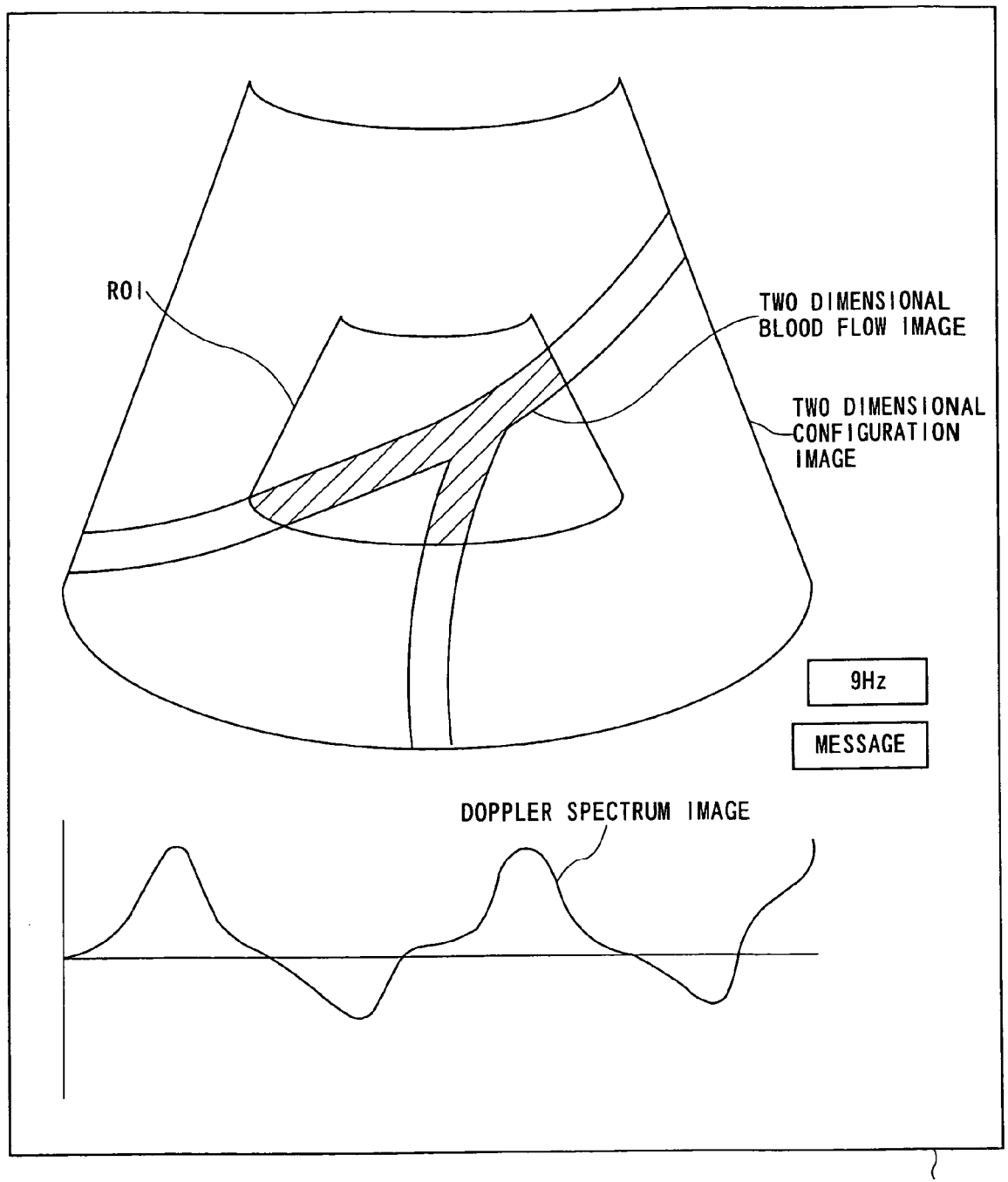
FIG. 3 is a diagram showing an example of a display on the monitor in the triplex mode.

The monitor 6 displays respective images processed by the image processing unit 5 simultaneously or substantially simultaneously. FIG. 3 shows an example of images displayed on the monitor 6 in the triplex mode. As shown in FIG. 3, in the triplex mode, a two dimensional blood flow image is overlaid on a ROI (region of interest) in a two dimensional configuration image and a Doppler spectrum image is displayed outside the two dimensional configuration image.

The operation panel 7 includes devices such as a keyboard, a trackball and a mouse. The operation panel 7 is used by an operator to switch modes, change the position or range of the ROI, and input a change of a point to collect a Doppler spectrum. The operation panel 7 is also used by the operator to input a threshold of a frame rate and functions as a setting unit to store the threshold in a threshold memory 8a (described below).

The control unit 8 includes a sequencer 84 and a computer having a CPU (Central Processing Unit) 81, an RAM (random-access memory) 82 and an HDD (hard disk drive) 83. The HDD 83 stores a control program for the ultrasonic diagnostic apparatus 1. In the control unit 8, the CPU 81 executes calculation based on a control program of the ultrasonic diagnostic apparatus while adequately storing a calculation result in the RAM 82. Based on the calculation result, the sequencer 84 is allowed to control each unit.

Figure 2:
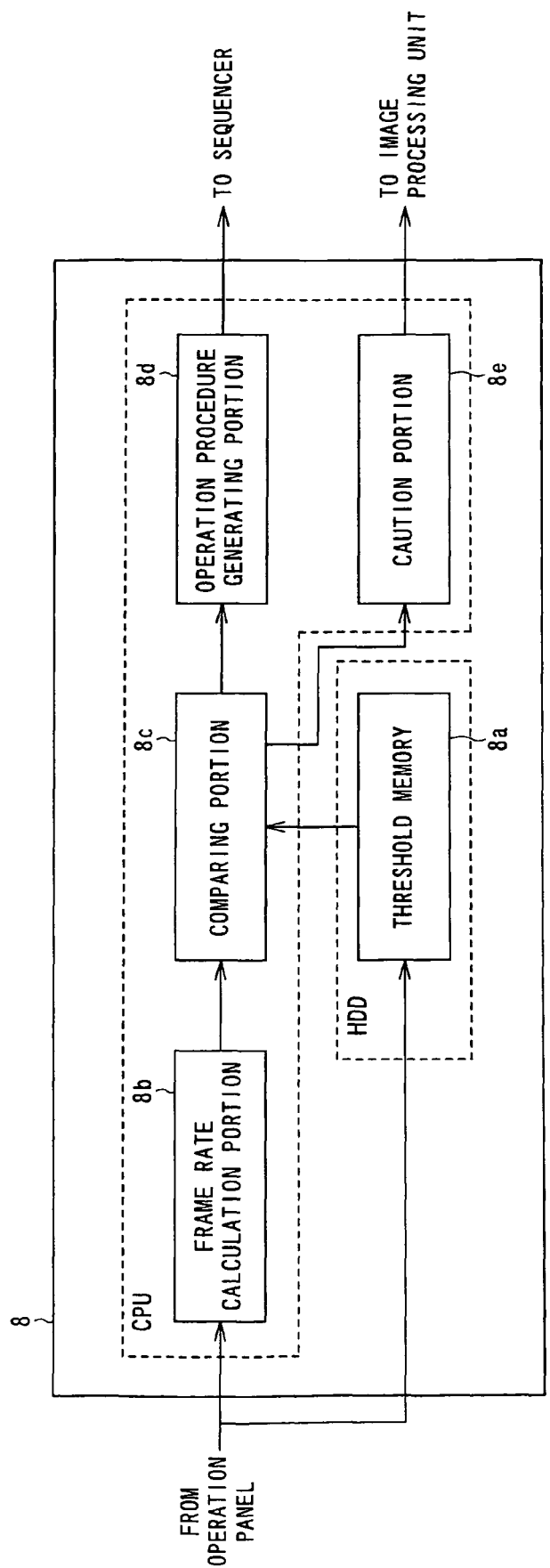
FIG. 2 is a functional block diagram of the control unit included in the ultrasonic diagnostic apparatus shown in FIG. 1.

FIG. 2 is a functional block diagram of the control unit 8 included in the ultrasonic diagnostic apparatus shown in FIG. 1. As shown in FIG. 2, the control unit 8 includes the threshold memory 8a, a frame rate calculation portion 8b, a comparing portion 8c, an operation procedure generating portion 8d and a caution portion 8e. The control unit 8 generates a procedure of an operation performed by each unit in accordance with a frame rate and allows a memory (not shown) in the sequencer 84 to store the operation procedure. Accordingly, each unit is allowed to perform scanning or signal processing in accordance with the operation procedure. The operation procedure is changed by an operation procedure generating portion 8d and set to the sequencer 84.

The operation procedure generating portion 8d generates an operation procedure. As shown in FIGS. 4 to 7, the operation procedure specifies a scanning sequence to generate each image and also specifies timing and direction of transmission/reception of ultrasonic waves to generate each image in scanning of an object. Also, the operation procedure specifies an operation to the transmission/reception unit 3 and the signal processing unit 4. The operation specifications of the transmission/reception unit 3 include a specification of the number of transmission pulses. The operation specifications of the signal processing unit 4 specify which mode of processing units 41, 42, and 43 performs an operation at which timing. In particular, the operation specifications specify a filter bandwidth of the wall filter to the color Doppler mode processing unit 42 and specify the classification of values obtained from a signal. This operation procedure is generated based on setting of the density of scanning lines, the number of ensemble, and the pulse repetition frequency of a two dimensional configuration image, a two dimensional blood flow image, and a Doppler spectrum image. In a normal state where priority need not be placed on a frame rate, the operation procedure is generated by a predetermined normal generation routine.

When the frame rate is compared with a predetermined threshold and when the frame rate is lower than the threshold, the operation procedure generating portion 8d generates an operation procedure to maintain the frame rate and compulsorily rewrites the memory of the sequencer 84. When the frame rate increases to exceed the threshold, the compulsory change stops and the operation procedure generated according to a rule is performed again.

When the operation procedure is changed to maintain the frame rate, the number of ensemble of transmission/reception of ultrasonic waves in CFM mode scanning is reduced and transmission/reception of ultrasonic waves in B mode scanning is sequentially pushed forward to the time generated by the decrease in the number of ensemble of the CFM mode scanning. That is, the operation procedure generating portion 8d functions as a scanning sequence setting unit to change the scanning sequence to a scanning sequence in which the number of ensemble of transmission/reception of ultrasonic waves in the CFM mode scanning is decreased.

The number of ensemble after change may be set to a predetermined number or may be adjusted in accordance with a decrease in the frame rate. When the predetermined number is set, an operation procedure including the predetermined number of ensemble as an operation procedure for maintaining the frame rate is stored in the HDD 83 as part of the control program of the ultrasonic diagnostic apparatus or a LUT (Look Up Table). When the number of ensemble is adjusted, the number of ensemble is decreased depending on a decrease in the frame rate so as to generate the operation procedure.

Figure 4:
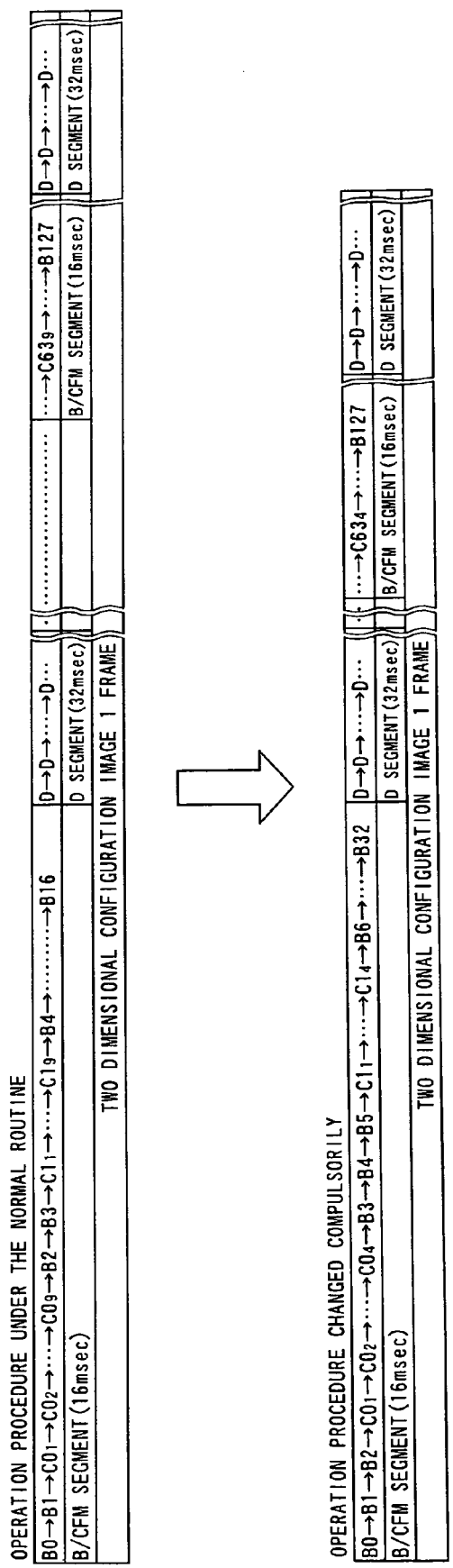
FIG. 4 is a diagram explaining alteration of an operation procedure according to the first embodiment.

FIG. 4 illustrates a change of the operation procedure to maintain the frame rate, performed by the operation procedure generating portion 8d. In FIG. 4, "B0" specifies to perform B mode scanning on a scanning line of number 0 and also specifies to perform B mode signal processing in the B mode processing unit 41 in signal processing unit. "C01" specifies to perform first transmission/reception of ultrasonic waves of CFM mode scanning on the scanning line of number 0 and also specifies to perform CFM mode signal processing in the color Doppler mode processing unit 42 in signal processing unit so as to obtain first data of auto correlation processing. "D" specifies to perform D mode scanning in a predetermined region of interest and also specifies to perform D mode signal processing in the D mode processing unit 43 in signal processing unit.

As shown in FIG. 4, by compulsorily changing the operation procedure, a scanning sequence where transmission/reception of ultrasonic waves is performed nine times on the same scanning line in CFM mode scanning and then the next scanning line is scanned in B mode scanning is changed to a scanning sequence where transmission/reception of ultrasonic waves is performed four times on the same scanning line and then B mode scanning is performed. In other words, the number of ensemble in CFM mode scanning is compulsorily reduced from nine to four in the scanning sequence.

The frame rate compared with the predetermined threshold is calculated by the frame rate calculation portion 8b. The frame rate is calculated based on the assumption that the operation procedure is generated by the normal generation routine regardless of whether the operation procedure is changed to maintain the frame rate.

The frame rate means the number of frames that can be generated in one second. That is, when time of each transmission/reception in B mode scanning, CFM mode scanning, and D mode scanning is represented by B, C, and D, respectively, the number of scanning lines in B mode scanning is represented by Nb, the number of scanning lines in CFM mode scanning is represented by Nc, the number of ensemble in CFM mode scanning is represented by Ec, and the number of times of D mode scanning performed during B mode scanning of one frame is represented by M, the frame rate is $1/(B*Nb+C*N_c*Ec+D*M)$ (fps). In a case of Doppler segment scanning, $D*M \geq 2*(B*Nb+C*Nc*Ec)$ should be satisfied.

The frame rate is calculated when the control program of the ultrasonic diagnostic apparatus is started by an operation causing a change in the frame rate, such as a change in range or depth of a two dimensional blood flow image or a change in collecting point or range for forming a Doppler spectrum image. Alternatively, calculation of the frame rate can constantly be performed.

The predetermined threshold compared with the frame rate is stored in the threshold memory 8a. This threshold is a threshold of the frame rate causing a change in the operation procedure and is stored in the threshold memory 8a by the operator operating the operation panel 7. The stored threshold is a value desired by the operator, but should desirably be about 3 fps, which is a minimum value enabling an accurate observation of an object in diagnosis. That is, the operation panel 7 functions as a change accepting unit to accept a change of the threshold of the frame rate from the operator.

The frame rate is compared with the threshold in the comparing portion 8c. That is, the comparing portion 8c functions as a comparing unit to compare the threshold stored in the threshold memory 8a with the frame rate calculated by the frame rate calculation portion 8b.

The caution portion 8e functions as a caution unit to give a notice prior to a change of the operation procedure for maintaining the frame rate. For this function, a threshold for caution to define a condition of giving a caution is set in advance and is stored in the threshold memory 8a. The threshold for caution is read into the comparing portion 8c like the threshold used to determine whether the operation procedure should be changed and is compared with the frame rate calculated by the frame rate calculation portion 8b.

When the comparing portion 8c determines that the frame rate calculated by the frame rate calculation portion 8b is equal to or lower than the threshold for caution, the comparing portion 8c notifies the caution portion 8e of the determination. In response to this, the caution portion 8e generates caution information of voice, text, or figures, and allows a predetermined output device to output the caution information.

FIG. 2 shows an example in which the caution portion 8e generates text information as caution information. In this case, the caution portion 8e transmits the caution information to the image processing unit 5. Accordingly, the caution information is converted by the image processing unit 5 into image data that can be displayed on the monitor 6 and is eventually displayed on the monitor 6. FIG. 3 shows an example in which a desired message as caution information is displayed near the frame rate displayed together with the two dimensional configuration image.

The caution information may be color information indicated by changing the color of characters, figures, or images displayed on the monitor 6, or may be display information indicated by blinking the characters, figures, or images.

By seeing the caution information displayed on the monitor 6, the operator can know in advance that the operation procedure will be changed soon. Further, the operator can change the frame rate or reset the threshold for changing the operation procedure as necessary. Note that, the caution information needs to be notified to the operator before the operation procedure is changed, and thus the threshold for caution is set to a higher value than the threshold for changing the operation procedure.

According to the operation procedure generated to maintain the frame rate by the control unit 8, the number of times of transmission/reception of ultrasonic waves in CFM mode scanning decreases and the number of times of transmission/reception of ultrasonic waves in B mode scanning increases in one B/CFM segment, and the number of B/CFM segments in one frame of a two dimensional configuration image and a two dimensional blood flow image decreases in the scanning sequence. Accordingly, time required for forming one frame of the two dimensional configuration image and the two dimensional blood flow image becomes shorter. That is, by setting the threshold to a lower limit of the frame rate that enables observation of an object, the frame rate can be kept above the lower limit, so that the operator can realizably observe an object.

Figure 12:
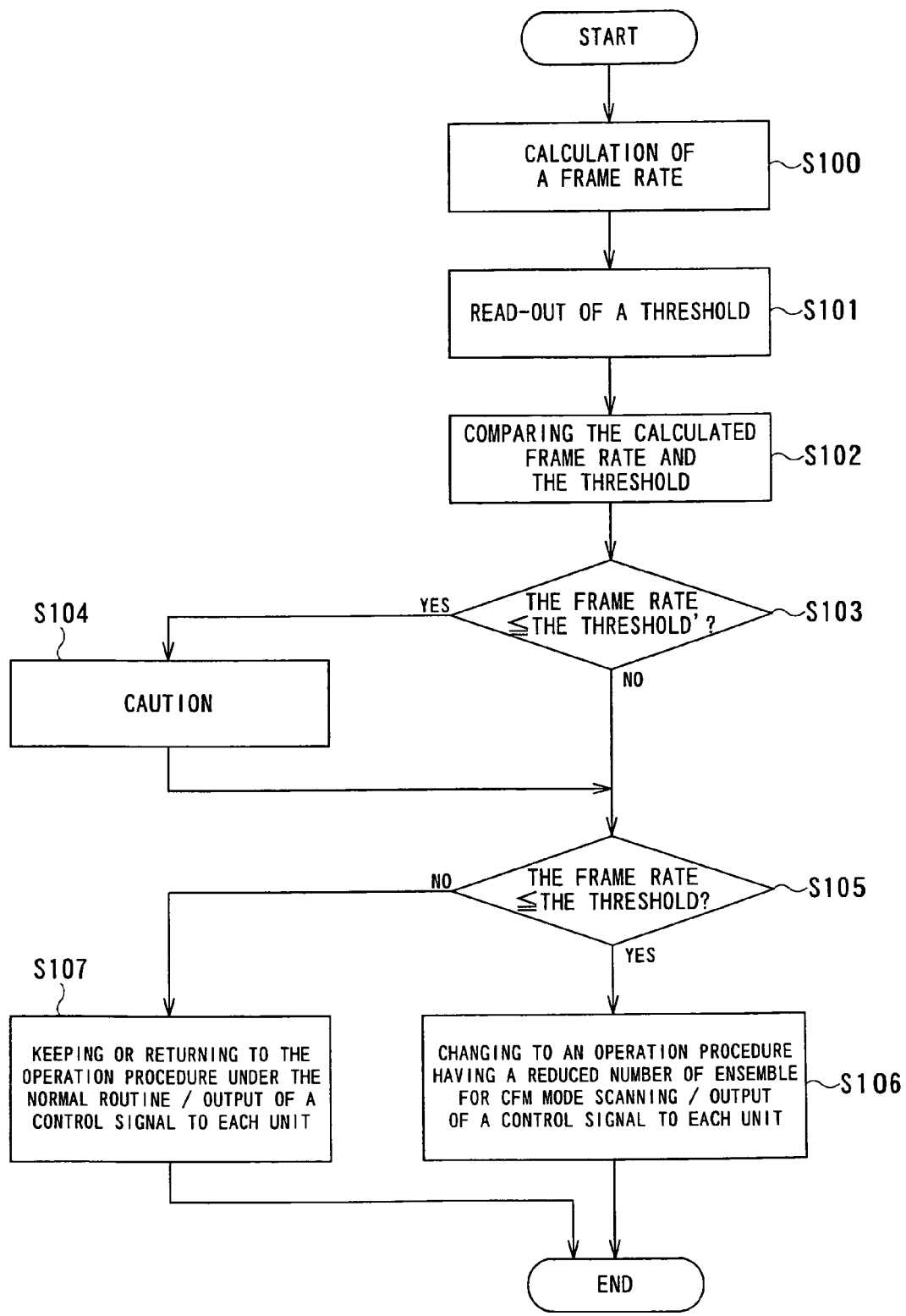
FIG. 12 is a flowchart showing operation of the ultrasonic diagnostic apparatus according to the first embodiment.

Now, an operation of the ultrasonic diagnostic apparatus 1 is described with reference to FIG. 12.

The operator inputs a threshold for changing the operation procedure and a threshold for caution through the operation panel 7 of the ultrasonic diagnostic apparatus 1 and stores the input thresholds in the threshold memory 8a in advance. More specifically, the operator sets a lower limit of the frame rate at which an object can be accurately observed as the threshold for changing the operation procedure and stores it in the threshold memory 8a. Also, the operator sets a frame rate corresponding to the timing of giving a caution prior to a change of the operation procedure as the threshold for caution and stores it in the threshold memory 8a.

Then, the frame rate calculation portion 8b of the control unit 8 calculates a frame rate (S100). Then, the comparing portion 8c reads the threshold for changing the operation procedure and the threshold for caution (hereinafter referred to as threshold') from the threshold memory 8a (S101). The comparing portion 8c compares the frame rate calculated by the frame rate calculation portion 8b with the threshold for changing the operation procedure and also compares the frame rate calculated by the frame rate calculation portion 8b with the threshold' for caution (S102).

Herein, when the operator performs input causing a change of the frame rate through the operation panel 7, the changed frame rate may be below the set threshold depending on the degree of the change.

When the comparing portion 8c determines that the frame rate is equal to or lower than the threshold' for caution (YES in S103), the comparing portion 8c notifies the caution portion 8e that the frame rate is equal to or lower than the threshold' for caution. In response to this, the caution portion 8e generates caution information and transmits it to the image processing unit 5 (S104). As a result, the caution information is displayed on the monitor 6.

The operator checks the caution information displayed on the monitor 6, so that the operator can know in advance that the operation procedure will be changed if the frame rate further decreases. The operator can increase the frame rate or can reset the threshold for changing the operation procedure to a lower value in accordance with the caution information.

If the frame rate further decreases, the comparing portion 8c determines that the frame rate is equal to or lower than the threshold for changing the operation procedure (YES in S105). Under such a frame rate, an object cannot be accurately observed in many cases. Therefore, the operation procedure generating portion 8d changes the operation procedure to maintain the frame rate.

As shown in FIG. 4, the operation procedure generating portion 8d generates an operation procedure realizing a scanning sequence having a reduced number of ensemble in transmission/reception of ultrasonic waves in CFM mode scanning, so as to compulsorily rewrite the memory of the sequencer 84. The sequencer 84 outputs a control signal according to the compulsorily changed operation procedure to each unit (S106). The transmission/reception unit 3 and the ultrasonic probe 2 perform transmission/reception of ultrasonic waves with a reduced number of ensemble in CFM mode scanning based on the changed operation procedure.

On the other hand, when the frame rate exceeds the threshold' for caution, caution information is not generated (No in S103). When the frame rate exceeds the threshold for changing the operation procedure (No in S105), the set operation procedure is maintained or returned to the operation procedure generated under the normal generation routine so as to recover the scanning sequence (S107).

Figure 8:
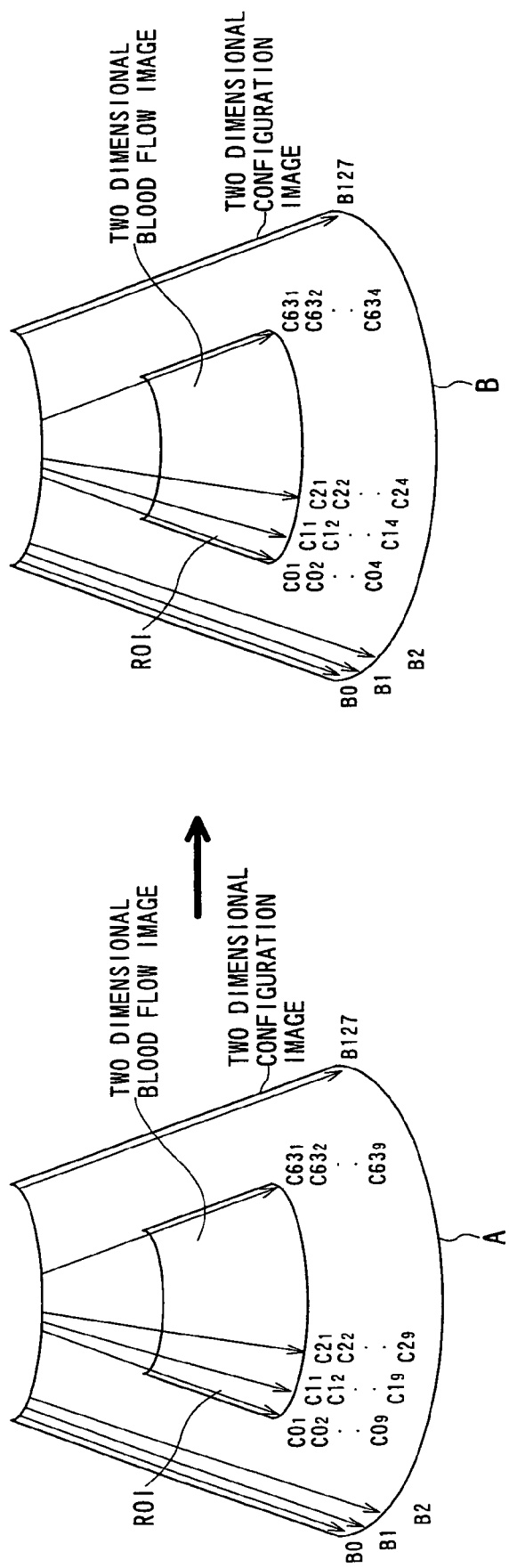
FIG. 8 is a diagram showing scanning under an operation procedure for performing a scanning sequence having a reduced number of ensembles.

FIG. 8 illustrates a comparison between scanning A according to the operation procedure generated by the normal generation routine and scanning B according to the operation procedure changed to maintain the frame rate. D mode scanning is not shown in this figure. As shown in FIG. 8, in the changed operation procedure, the number of times of transmission/reception of ultrasonic waves in the same scanning line in CFM mode scanning is reduced in the scanning sequence, so that the time required to scan an entire scanning area to generate a configuration image and a blood flow image can be shortened. Accordingly, even when the operator decreases the frame rate in the triplex mode or the like shown in FIG. 4, a frame rate at which an object can be observed can be maintained.

Furthermore, by allowing the operator to set the threshold through the operation panel 7 and store the threshold in the threshold memory 8a, the scanning sequence can be changed to be adapted to a usage purpose of the operator and enhanced convenience can be obtained.

2. Second Embodiment

A second embodiment of the present invention will be described. A structure of an ultrasonic diagnostic apparatus according to the second embodiment is equivalent to that according to the first embodiment shown in FIGS. 1 and 2. Therefore, detail description of structure is omitted.

According to a second embodiment, when the frame rate is below the threshold, the operation procedure generating portion 8d generates an operation procedure specifying a scanning sequence in which the density of scanning lines is decreased in transmission/reception of ultrasonic waves in CFM mode scanning, in order to maintain the frame rate.

The operation procedure generating portion 8d generates an operation procedure specifying a scanning sequence in which the density of scanning lines of transmission/reception of ultrasonic waves in CFM mode scanning is decreased and B mode scanning is pushed forward in the generated time. Accordingly, in the B/CFM segment, the number of times of transmission/reception of ultrasonic waves in B mode scanning increases, the time required to scan an entire scanning area in B mode scanning and CFM mode scanning is shortened, and thus one frame of a two dimensional configuration image and a two dimensional blood flow image can be formed more quickly.

When the density of scanning lines is decreased in CFM mode scanning, the density may be changed to a predetermined density or may be adjusted depending on a decrease in the frame rate.

Figure 5:
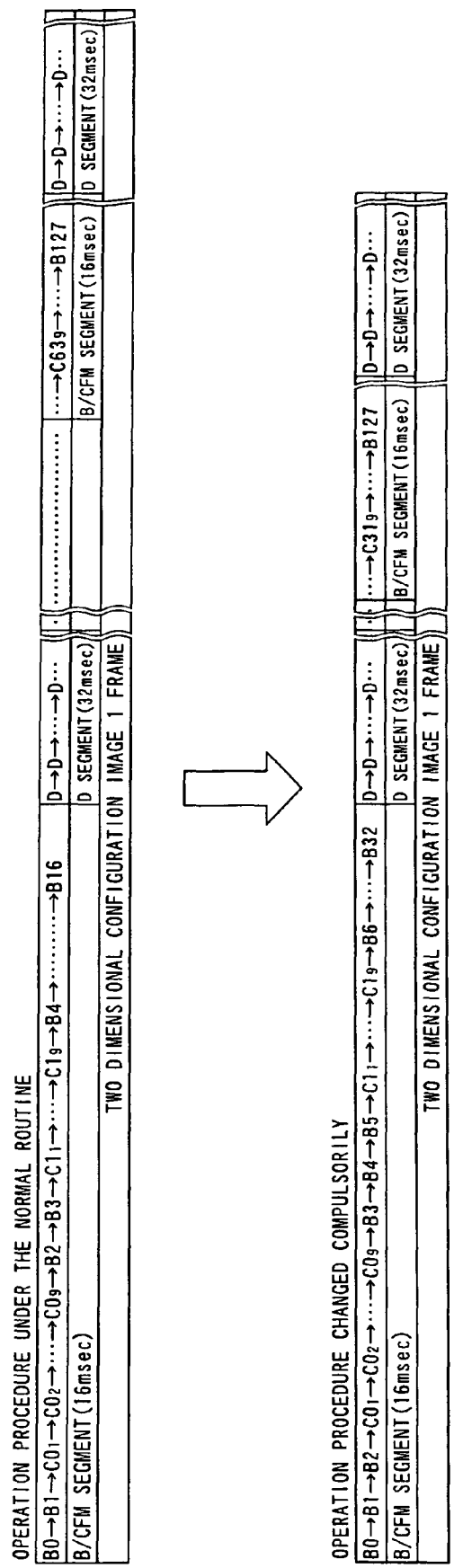
FIG. 5 is a diagram explaining alteration of an operation procedure according to the second embodiment.

FIG. 5 is a diagram explaining alteration of an operation procedure for keeping a frame rate by the operation procedure generating portion 8d.

As shown in FIG. 5, the operation procedure generating portion 8d changes the operation procedure to an operation procedure specifying a scanning sequence in which the density of scanning lines is decreased by, for example, thinning the scanning lines from 64 to 32 in CFM mode scanning, and B mode scanning is pushed forward to the time generated by the thinning.

Figure 13:
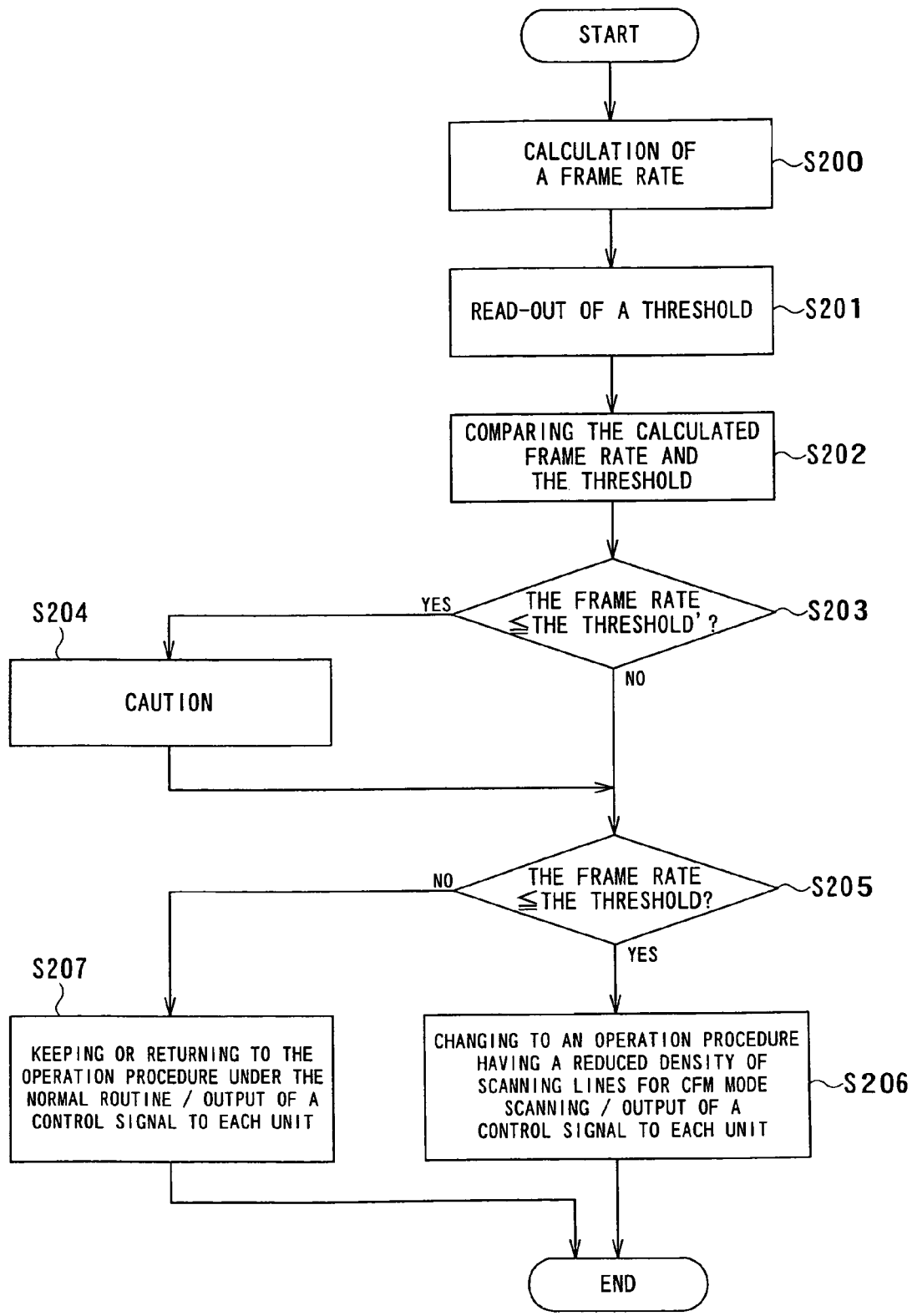
FIG. 13 is a flowchart showing operation of the ultrasonic diagnostic apparatus according to the second embodiment.

Now, an operation of the ultrasonic diagnostic apparatus 1 is described with reference to FIG. 13.

The frame rate calculation portion 8b of the control unit 8 calculates a frame rate (S200). Then, the comparing portion 8c reads the threshold for changing the operation procedure and the threshold' for caution from the threshold memory 8a (S201). The comparing portion 8c compares the frame rate calculated by the frame rate calculation portion 8b with the threshold for changing the operation procedure and also compares the frame rate calculated by the frame rate calculation portion 8b with the threshold' for caution (S202).

When the comparing portion 8c determines that the frame rate is equal to or lower than the threshold' for caution (YES in S203), the comparing portion 8c notifies the caution portion 8e that the frame rate is equal to or lower than the threshold' for caution. In response to this, the caution portion 8e generates caution information and transmits it to the image processing unit 5 (S204). As a result, the caution information is displayed on the monitor 6.

If the frame rate further decreases, the comparing portion 8c determines that the frame rate is equal to or lower than the threshold for changing the operation procedure (YES in S205). Accordingly, the comparing portion 8c allows the operation procedure generating portion 8d to change the operation procedure to maintain the frame rate.

The operation procedure generating portion 8d newly generates an operation procedure specifying a scanning sequence in which the scanning density is decreased in transmission/reception of ultrasonic waves in CFM mode scanning and B mode scanning is pushed forward accordingly, as shown in FIG. 5. The sequencer 84 outputs a control signal according to the compulsorily changed operation procedure to each unit (S206). Particularly, the ultrasonic probe 2 and the transmission/reception unit 3 realize a scanning sequence in which the density of scanning lines is decreased in transmission/reception of ultrasonic waves in CFM mode scanning in accordance with the changed operation procedure.

On the other hand, when the frame rate exceeds the threshold for changing the operation procedure (No in S205), the operation procedure is maintained or returned to the operation procedure generated under the normal generation routine so as to recover the scanning sequence (S207). Furthermore, when the frame rate exceeds the threshold' for caution (No in S203), caution information is not generated to be displayed.

Figure 9:
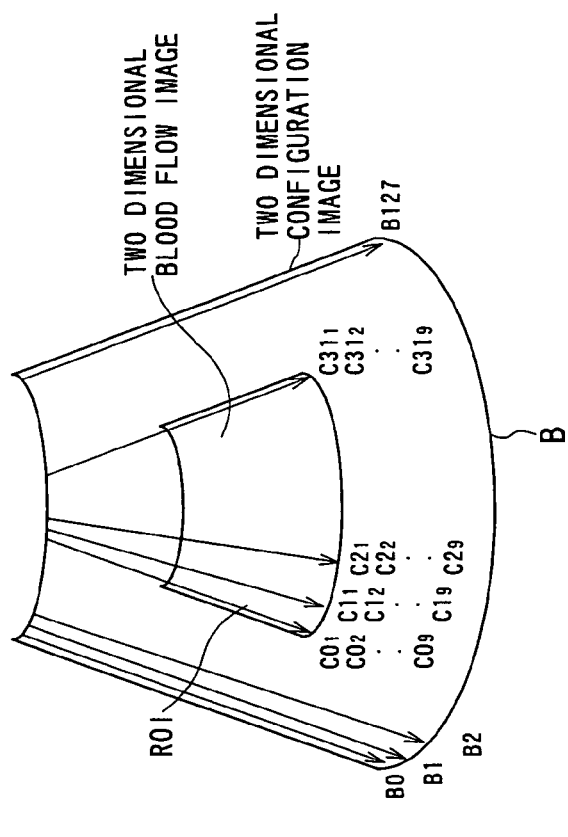
FIG. 9 is a diagram showing scanning under an operation procedure for performing a scanning sequence having a reduced density of scanning lines.
Figure 9:
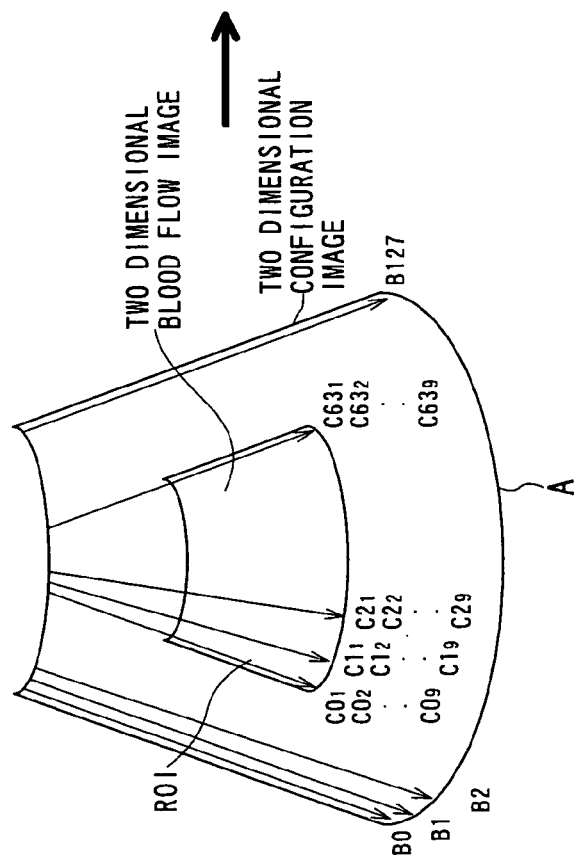

FIG. 9 illustrates a comparison between scanning A according to the operation procedure generated by the normal generation routine and scanning B according to the operation procedure changed to maintain the frame rate. Under the changed operation procedure, the density of scanning lines in CFM mode scanning, that is, the number of scanning lines in a predetermined area decreases in a scanning sequence, and thus the time required to scan an entire area to form a configuration image and a blood flow image can be shortened. Accordingly, a favorable frame rate can be maintained in the triplex mode or the like shown in FIG. 4.

3. Third Embodiment

A third embodiment of the present invention will be described. A structure of an ultrasonic diagnostic apparatus according to the third embodiment is equivalent to that according to the first embodiment shown in FIGS. 1 and 2. Therefore, detail description of structure is omitted.

In the ultrasonic diagnostic apparatus 1 according to a third embodiment, the operation procedure generating portion 8d changes the operation procedure of performing CFM mode signal processing to an operation procedure of performing P mode signal processing for generating a two dimensional blood flow image by a power Doppler mode. The power Doppler mode is a mode of displaying blood flow by detecting a Doppler shift and then obtaining a blood flow power value calculated based on the Doppler shift.

When the comparing portion 8c determines that the frame rate is lower than the threshold, the operation procedure generating portion 8d generates an operation procedure of specifying the color Doppler mode processing unit 42 to generate data of a two dimensional blood flow image based on the blood flow power value, in other words, to perform P mode signal processing, and writes the operation procedure in the memory of the sequencer 84. The sequencer 84 outputs a control signal to the calculation portion 42d of the color Doppler mode processing unit 42 in order to allow it to perform P mode signal processing. The calculation portion 42d performs calculation based on the blood flow power value in accordance with the operation procedure specified to obtain the blood flow power value in the signal processing. That is, the operation procedure generating portion 8d functions as a blood flow image generation control unit to allow the color Doppler signal processing unit 42 to detect a blood flow power value from an echo signal and to generate a blood flow image based on the blood flow power value.

Figure 6:
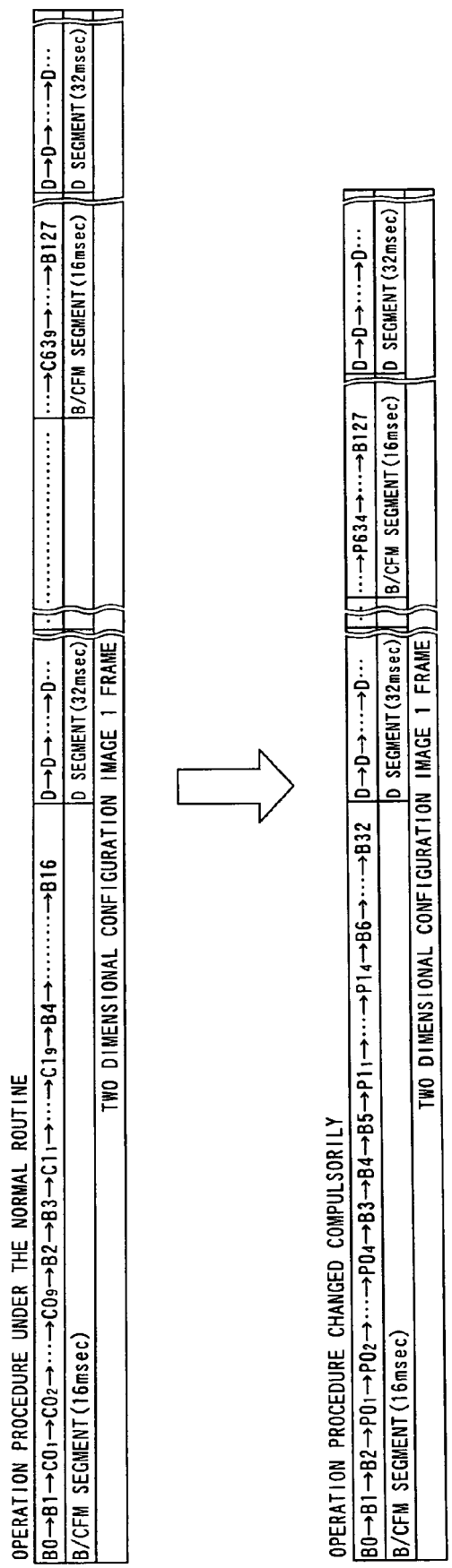
FIG. 6 is a diagram explaining alteration of an operation procedure according to the third embodiment.

FIG. 6 is a diagram explaining alteration of an operation procedure for keeping a frame rate by the operation procedure generating portion 8d.

As shown in FIG. 6, CFM mode signal processing is switched to P mode signal processing. That is, the operation procedure is compulsorily changed to an operation procedure of specifying the calculation portion 42d to perform calculation by obtaining a blood flow power value. Further, when a two dimensional blood flow image is generated based on a blood flow power value, a reduced number of ensemble has only a little effect thereon. Therefore, the operation procedure is compulsorily changed to an operation procedure of specifying a scanning sequence having a reduced number of ensemble.

Figure 14:
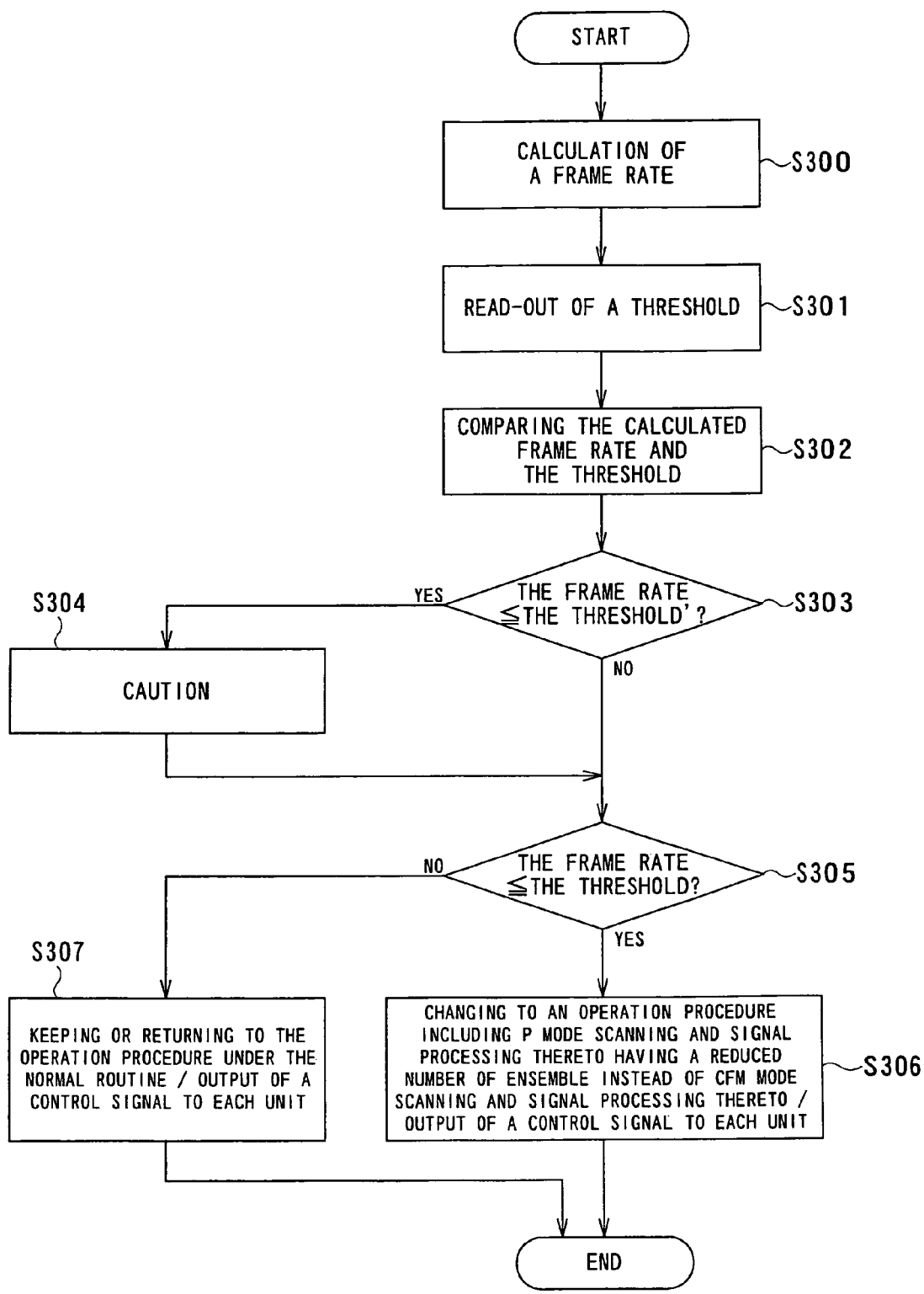
FIG. 14 is a flowchart showing operation of the ultrasonic diagnostic apparatus according to the third embodiment.

Now, an operation of the ultrasonic diagnostic apparatus 1 is described with reference to FIG. 14.

The frame rate calculation portion 8b of the control unit 8 calculates a frame rate (S300). Then, the comparing portion 8c reads the threshold for changing the operation procedure and the threshold' for caution from the threshold memory 8a (S301). The comparing portion 8c compares the frame rate calculated by the frame rate calculation portion 8b with the threshold for changing the operation procedure and also compares the frame rate calculated by the frame rate calculation portion 8b with the threshold' for caution (S302).

When the comparing portion 8c determines that the frame rate is equal to or lower than the threshold' for caution (YES in S303), the comparing portion 8c notifies the caution portion 8e that the frame rate is equal to or lower than the threshold' for caution. In response to this, the caution portion 8e generates caution information and transmits it to the image processing unit 5 (S304). As a result, the caution information is displayed on the monitor 6.

If the frame rate further decreases, the comparing portion 8c determines that the frame rate is equal to or lower than the threshold for changing the operation procedure (YES in S305). Accordingly, the comparing portion 8c allows the operation procedure generating portion 8d to change the operation procedure to maintain the frame rate.

The operation procedure generating portion 8d performs P mode signal processing, generates an operation procedure having a reduced number of ensemble, and compulsorily rewrites the memory of the sequencer 84 (S306). The sequencer 84 outputs a control signal according to the operation procedure to each unit. Particularly, the calculation portion 42d shifts to P mode signal processing of obtaining a blood flow power value according to the operation procedure and performs calculation to obtain a blood flow power value.

On the other hand, when the frame rate exceeds the threshold for changing the operation procedure (No in S305), the operation procedure is maintained or returned to the operation procedure generated under the normal generation routine so as to recover the scanning sequence (S307). Furthermore, when the frame rate exceeds the threshold' for caution (No in S303), caution information is not generated to be displayed.

Figure 10:
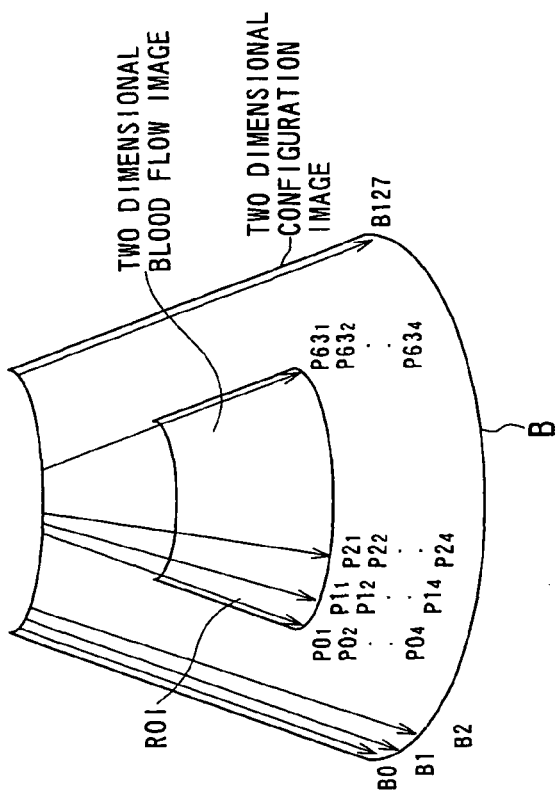
FIG. 10 is a diagram showing scanning under an operation procedure providing scanning and signal processing on power Doppler mode.
Figure 10:
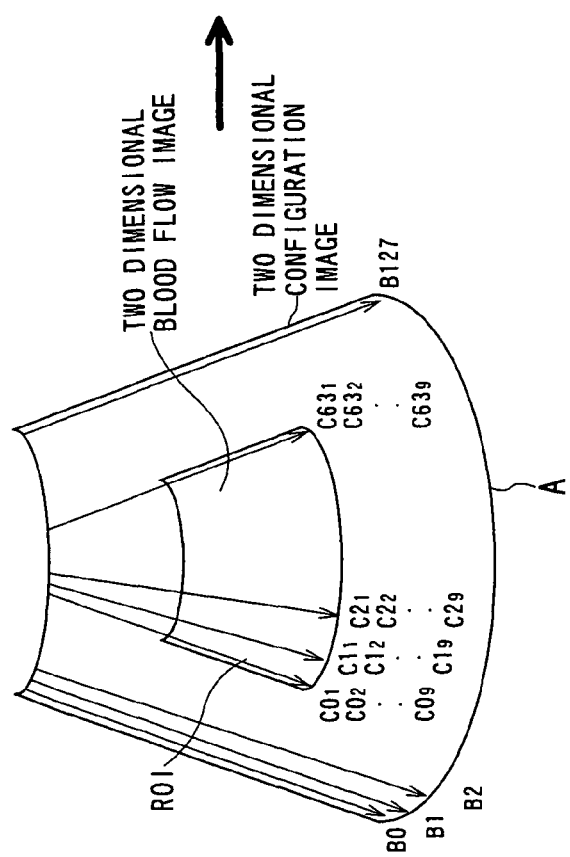

FIG. 10 illustrates a comparison between scanning A according to the operation procedure generated by the normal generation routine and scanning B according to the operation procedure changed to maintain the frame rate. In the figure, "P" denotes a specification to perform P mode signal processing in signal processing. As shown in FIG. 10, in the changed operation procedure, the number of ensemble is smaller than that in CFM mode scanning and the time required to scan an entire scanning area to form a configuration image and a blood flow image is shortened.

With this operation, even when a change causing a decrease in the frame rate occurs during the operation of the ultrasonic diagnostic apparatus 1, the frame rate at which an object can be observed can be maintained by using a power Doppler mode capable of displaying images at a relatively high frame rate.

4. Forth Embodiment

A forth embodiment of the present invention will be described. A structure of an ultrasonic diagnostic apparatus according to the forth embodiment is equivalent to that according to the first embodiment shown in FIGS. 1 and 2. Therefore, detail description of structure is omitted.

In the ultrasonic diagnostic apparatus 1 according a fourth embodiment, the operation procedure generating portion 8d changes the operation procedure to an operation procedure using a dynamic flow.

The dynamic flow is a mode described in U.S. Pat. No. 6,508,766 which corresponds to Japanese Patent Application (Laid-Open) No. 2001-269344, for example. In the dynamic flow, this embodiment adopts a change of reducing the number of ensemble and obtaining a two dimensional blood flow image based on a blood flow power value, a change of a filter bandwidth of the wall filter 42b, and a change of the number of transmission pulses.

That is, in the ultrasonic diagnostic apparatus 1 according to this embodiment, an operation procedure of generating a blood flow image indicating blood flow information in color is adopted when the number of ensemble is equal to or larger than a predetermined value. On the other hand, when the number of ensemble is equal to or smaller than the predetermined value, an operation procedure of generating a blood flow image indicating blood flow information by luminance according to a blood flow power value (dynamic flow mode) is adopted.

Figure 7:
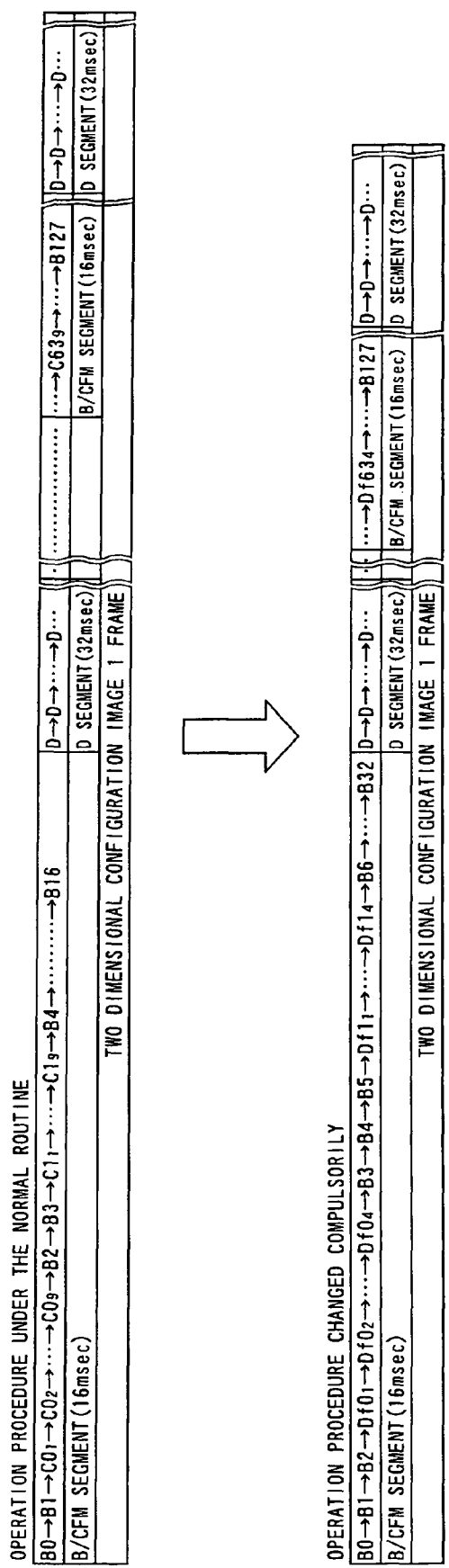
FIG. 7 is a diagram explaining alteration of an operation procedure according to the forth embodiment.

FIG. 7 is a diagram explaining alteration of an operation procedure for keeping a frame rate by the operation procedure generating portion 8d.

As shown in FIG. 7, CFM mode signal processing is switched to Df mode signal processing to generate a two dimensional blood flow image based on the dynamic flow. The operation procedure is compulsorily changed to an operation procedure of allowing the calculation portion 42d to perform calculation based on a blood flow power value, widening the filter bandwidth of the wall filter 42b to realize an almost through state, and setting the number of transmission pulses of ultrasonic waves in transmission/reception of ultrasonic waves to 2 or less. That is, the operation procedure generating portion 8d also functions as a pulse control unit.

As a result of the change of the operation procedure performed by the operation procedure generating portion 8d, the blood flow image is changed from a color mode image to a luminance-displayed monochrome dynamic flow image. Accordingly, the operator can know in advance that the blood flow image will change from a color image to a monochrome image by seeing the caution information generated by the caution portion 8e.

Figure 15:
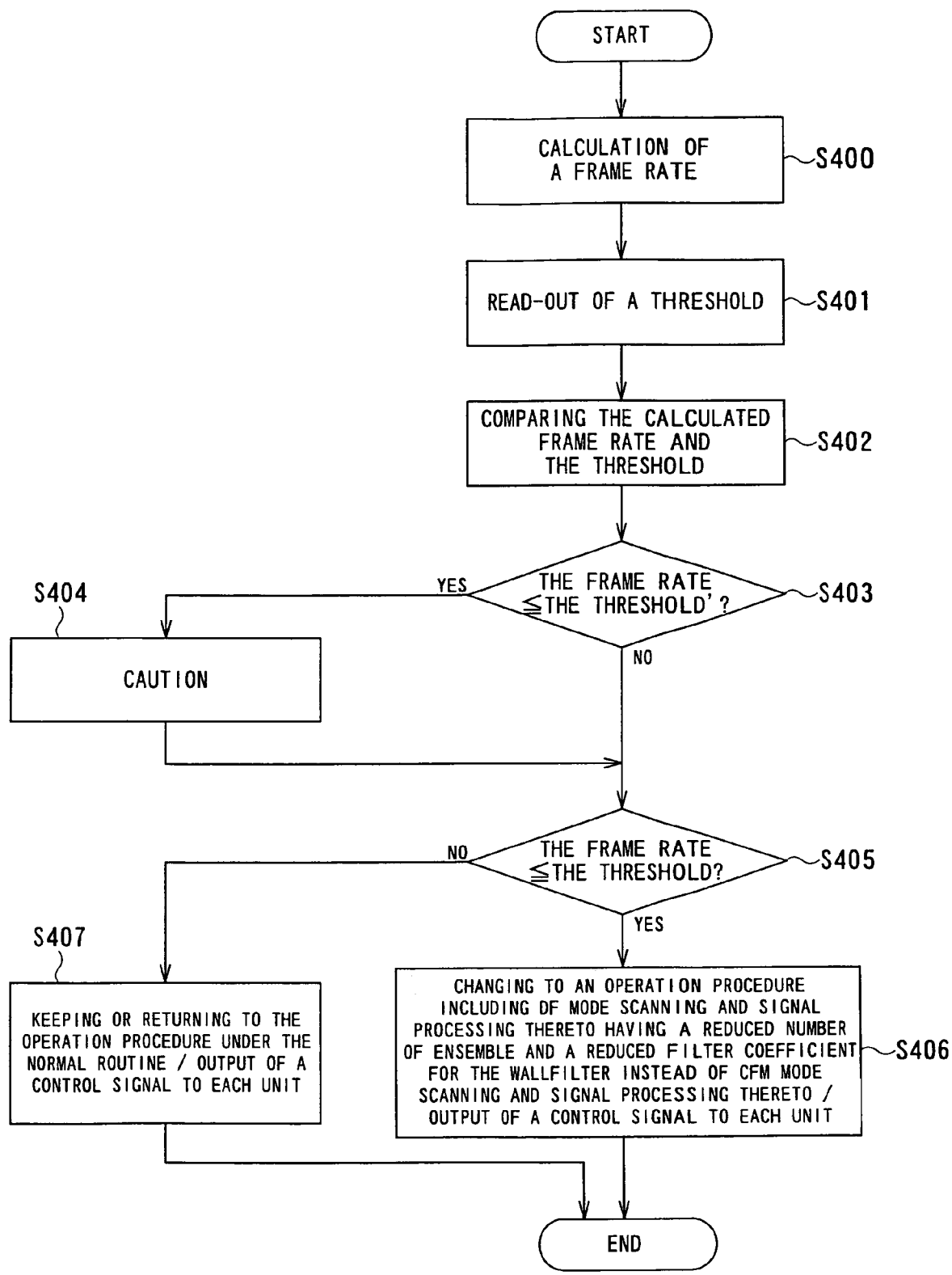
FIG. 15 is a flowchart showing operation of the ultrasonic diagnostic apparatus according to the forth embodiment.

Now, an operation of the ultrasonic diagnostic apparatus 1 is described with reference to FIG. 15.

The frame rate calculation portion 8b of the control unit 8 calculates a frame rate (S400). Then, the comparing portion 8c reads the threshold for changing the operation procedure and the threshold' for caution from the threshold memory 8a (S401). The comparing portion 8c compares the frame rate calculated by the frame rate calculation portion 8b with the threshold for changing the operation procedure and also compares the frame rate calculated by the frame rate calculation portion 8b with the threshold' for caution (S402).

When the comparing portion 8c determines that the frame rate is equal to or lower than the threshold' for caution (YES in S403), the comparing portion 8c notifies the caution portion 8e that the frame rate is equal to or lower than the threshold' for caution. In response to this, the caution portion 8e generates caution information and transmits it to the image processing unit 5 (S404). As a result, the caution information is displayed on the monitor 6.

If the frame rate further decreases, the comparing portion 8c determines that the frame rate is equal to or lower than the threshold for changing the operation procedure (YES in S405). Accordingly, the comparing portion 8c allows the operation procedure generating portion 8d to change the operation procedure to maintain the frame rate.

The operation procedure generating portion 8d generates an operation mode in which the number of ensemble is reduced and CFM mode signal processing is switched to Df mode signal processing and compulsorily rewrites the memory of the sequencer 84 (S406). The sequencer 84 transmits a control signal to each unit in accordance with this operation procedure. In particular, the ultrasonic probe 2 and the transmission/reception unit 3 perform transmission/reception of ultrasonic waves with two or less pulses in scanning for a two dimensional blood flow image. The calculation portion 42d performs calculation to obtain a blood flow power value. The wall filter 42b widens the filter bandwidth to realize an almost through state.

On the other hand, when the frame rate exceeds the threshold for changing the operation procedure (No in S405), the operation procedure is maintained or returned to the operation procedure generated under the normal generation routine so as to recover the scanning sequence (S407). Furthermore, when the frame rate exceeds the threshold' for caution (No in S403), caution information is not generated to be displayed.

Figure 11:
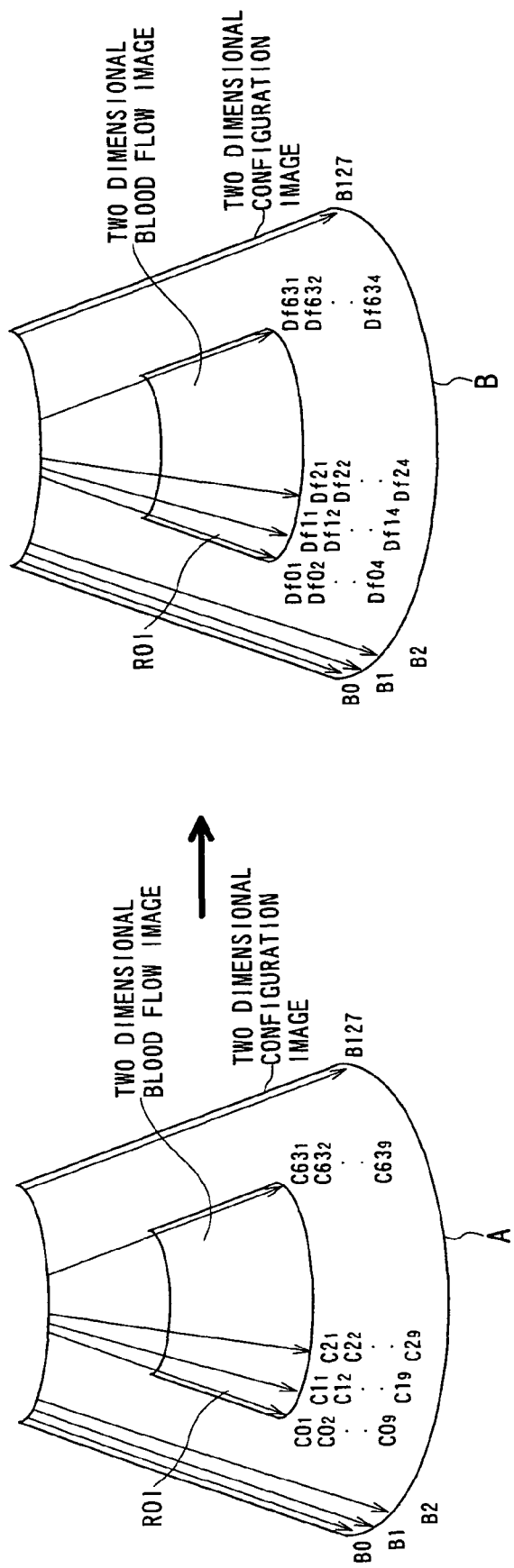
FIG. 11 is a diagram showing scanning under an operation procedure providing scanning and signal processing on dynamic flow.

FIG. 11 illustrates a comparison between scanning A according to the operation procedure generated based on the rule and scanning B according to the operation procedure changed to maintain the frame rate. In the figure, "Df" denotes Df mode signal processing. As shown in FIG. 11, in the changed operation procedure, the number of ensemble is smaller than in CFM mode scanning and the time required to scan an entire scanning area for a configuration image and a blood flow image is shortened.

Furthermore, in the Df mode signal processing, a favorable image can be obtained while maintaining a frame rate at which an object can be observed.

The configurations and operations for increasing the frame rate described in the first to fourth embodiments can be combined, so that the frame rate can be effectively increased. The combination may be set in accordance with a degree of change causing a decrease in the frame rate performed by the operator through the operation panel 7.

The operation procedure generating portion 8d generates an operation procedure having a reduced number of ensemble or an operation procedure having a reduced density of scanning lines by itself. However, the present invention is not limited to this manner. For example, an index specifying an address to construct an operation procedure and a parameter such as the number of ensemble may be transmitted to the sequencer 84 so that the sequencer 84 can construct an operation procedure in real time.

For example, when the number of ensemble in CFM mode scanning is reduced from 9 to 4, the operation procedure generating portion 8d may transmit an index and a parameter indicating that the number of ensemble in the CFM mode is 4 to the sequencer 84 so that the sequencer 84 can construct an operation procedure based on the index and the parameter.

In the above-described embodiments, the ultrasonic diagnostic apparatus 1 performs Doppler segmented scanning. However, the present invention can also be applied in Doppler interleaved scanning. Further, although a two dimensional configuration image and a two dimensional blood flow image have been mainly described in the above embodiments, the same effects can be obtained in a three dimensional configuration image and a three dimensional blood flow image and a three dimensional image mode can also be applied.

What is claimed is:

1. An ultrasonic diagnostic apparatus comprising:
a transmission and reception unit configured to transmit a first ultrasonic pulse and an ultrasonic pulse set including a plurality of second ultrasonic pulses corresponding to a number of ensembles on one scan line, and to receive a first echo signal corresponding to the first ultrasonic pulse and an echo signal set corresponding to the ultrasonic pulse set from an object;
a blood flow image generating unit configured to generate a blood flow image based on the first echo signals corresponding to a plurality of scan lines by processing including auto-correlation processing;
a Doppler spectrum image generating unit configured to generate a Doppler spectrum image based on the echo signal set;
a caution outputting unit configured to output caution information when a real frame rate of the blood flow images, which has been higher than a first predetermined frame rate, becomes equal to lower than the first predetermined frame rate; and
a scanning sequence setting unit configured to set up a first scanning sequence, including a first number of ensembles of the number of ensembles, for displaying the blood flow image and the Doppler spectrum image simultaneously substantially with mutual transmission and reception of the ultrasonic pulse set and the second ultrasonic pulse signal, and to alter the first scanning sequence to a second scanning sequence including a second number of ensembles which is smaller than the first number of ensembles when a real frame rate of the blood flow images, which has been higher than a second predetermined frame rate, which is lower than the first predetermined frame rate, becomes equal to or lower than the second predetermined frame rate, wherein
the caution outputting unit outputs the caution information before the scanning sequence setting unit alters the scanning sequences when the real frame rate has decreased.

2. An ultrasonic diagnostic apparatus according to claim 1, wherein the scanning sequence setting unit is configured to alter the first scanning sequence to the second scanning sequence according to transmission and reception of the ultrasonic pulse set if the real frame rate is to be under the predetermined frame rate.

3. An ultrasonic diagnostic apparatus according to claim 1, further comprising a blood-flow-image-generation control unit configured to control the blood flow image generating unit to detect blood flow power values from the first echo signal, and generate the blood flow image in accordance with the blood flow power values detected if the first number of ensembles is under a predetermined value.

4. An ultrasonic diagnostic apparatus according to claim 1, wherein the transmission and reception unit is configured to transmit the first ultrasonic pulse, the ultrasonic pulse set, and a third ultrasonic pulse, and receive the first echo signal, the echo signal set, and a third echo signal corresponding to the third ultrasonic pulse from the object, and
further comprising a configuration image generating unit configured to generate a configuration image showing a tissue of the object by luminance by subjecting the third echo signals corresponding to a plurality of scan lines to processing including envelope detection processing and logarithmic conversion processing, the configuration image being compounded with the blood flow image to be displayed.

5. An ultrasonic diagnostic apparatus according to claim 1, wherein the blood flow image generating unit is configured to generate the blood flow image so as to indicate blood flow information by colors if the first number of ensembles is beyond a predetermined value and generate the blood flow image so as to indicate the blood flow information by luminance if the first number of ensembles is under the predetermined value.

6. An ultrasonic diagnostic apparatus according to claim 1, further comprising an alteration receiving unit configured to receive alteration of the predetermined frame rate from an apparatus operator.

7. An ultrasonic diagnostic apparatus according to claim 3, further comprising a pulse control unit configured to set the number of pulse waves according to transmission of the first ultrasonic pulse as two and under value if the number of ensembles is under the predetermined value,
wherein the blood flow image generating unit includes a wall filter configured to eliminate a clutter component from the first echo signals,
the blood-flow-image-generation control unit being configured to control the blood flow image generating unit to extend a filter band of the wall filter if the number of ensembles is under the predetermined value.

8. An ultrasonic diagnostic method comprising:
setting up a first scanning sequence, including a first number of ensembles, for displaying a blood flow image and a Doppler spectrum image of an object simultaneously substantially with mutual transmission and reception;
transmitting a first ultrasonic pulse and an ultrasonic pulse set including a plurality of second ultrasonic pulses corresponding to a number of ensembles on one scan line in accordance with the scanning sequence, and receiving a first echo signal corresponding to the first ultrasonic pulse and an echo signal set corresponding to the ultrasonic pulse set from the object;
generating the blood flow image based on the first echo signals corresponding to a plurality of scan lines to processing including auto-correlation processing;
generating the Doppler spectrum image based on the echo signal;

outputting caution information when a real frame rate of the blood flow images, which has been higher than a first predetermined frame rate, becomes equal to or lower than the first predetermined frame rate; and altering the first scanning sequence to a second scanning sequence including a second number of ensembles which is smaller than the first number of ensembles if a real frame rate of the blood flow images, which has been higher than a second predetermined frame rate, which is lower than the first predetermined frame rate, becomes equal to or lower than the second predetermined frame rate, wherein the outputting outputs the caution information before the setting alters the scanning sequences when the real frame rate has decreased.

9. An ultrasonic diagnostic method according to claim 8, wherein the first scanning sequence is altered to the second scanning sequence according to transmission and reception of the ultrasonic pulse set if the real frame rate is to be under the predetermined frame rate.

10. An ultrasonic diagnostic method according to claim 8, wherein blood flow power values are detected from the first echo signal, and the blood flow image are generated in accordance with the blood flow power values detected if the first number of ensembles is under a predetermined value.

11. An ultrasonic diagnostic method according to claim 8, wherein the transmitting and receiving transmits the first ultrasonic pulse, the ultrasonic pulse set, and a third ultrasonic pulse, and receives the first echo signal, the echo signal set, and a third echo signal corresponding to the third ultrasonic pulse from the object, and further comprising generating a configuration image showing a tissue of the object by luminance by subjecting the third echo signals corresponding to a plurality of scan lines to processing including envelope detection processing and logarithmic conversion processing, the configuration image being compounded with the blood flow image to be displayed.

12. An ultrasonic diagnostic method according to claim 8, wherein the blood flow image are generated so as to indicate blood flow information by colors if the first number of ensembles is beyond a predetermined value and generated so as to indicate the blood flow information by luminance if the first number of ensembles is under the predetermined value.

13. An ultrasonic diagnostic method according to claim 8, further comprising receiving alteration of the predetermined frame rate from an apparatus operator.

14. An ultrasonic diagnostic method according to claim 10, further comprising setting the number of pulse waves according to transmission of the first ultrasonic pulse as two and under value and extending a filter band of a wall filter configured to eliminate a clutter component from the first echo signals if the first number of ensembles is under the predetermined value.

* * * * *